United States Patent
Ericson et al.

(10) Patent No.: US 6,716,814 B2
(45) Date of Patent: Apr. 6, 2004

(54) ENHANCING SOLUBILITY OF IRON AMINO ACID CHELATES AND IRON PROTEINATES

(75) Inventors: Clayton Ericson, Morgan, UT (US); H. DeWayne Ashmead, Fruit Heights, UT (US)

(73) Assignee: Albion International, Inc., Clearfield, UT (US)

( * ) Notice: Subject to any disclaimer, the term of this patent is extended or adjusted under 35 U.S.C. 154(b) by 0 days.

(21) Appl. No.: 09/931,397

(22) Filed: Aug. 16, 2001

(65) Prior Publication Data

US 2003/0069172 A1 Apr. 10, 2003

(51) Int. Cl.⁷ .............. A23J 3/30; A61K 38/01; C07F 15/02
(52) U.S. Cl. .............. 514/6; 426/656; 556/148
(58) Field of Search .............. 426/271, 656, 426/657; 435/68.1; 514/6, 21, 23, 53, 502; 536/121; 556/2.138, 148

(56) References Cited

U.S. PATENT DOCUMENTS

| | | | |
|---|---|---|---|
| 4,020,158 A | 4/1977 | Ashmead et al. | 514/6 |
| 4,167,564 A | 9/1979 | Jensen | 514/6 |
| 4,216,143 A | 8/1980 | Ashmead | 530/400 |
| 4,216,144 A | 8/1980 | Ashmead | 530/345 |
| 4,599,152 A | 7/1986 | Ashmead | 205/435 |
| 4,725,427 A | 2/1988 | Ashmead et al. | 514/23 |
| 4,774,089 A | 9/1988 | Ashmead | 514/6 |
| 4,830,716 A | 5/1989 | Ashmead | 556/50 |
| 4,863,898 A | 9/1989 | Ashmead et al. | 514/6 |
| 5,061,815 A | 10/1991 | Leu | 556/118 |
| 5,504,055 A | 4/1996 | Hsu | 504/121 |
| 5,516,925 A * | 5/1996 | Pederson et al. | 556/50 |
| 6,197,815 B1 | 3/2001 | Hsu | 514/502 |

FOREIGN PATENT DOCUMENTS

WO 98/48648 * 11/1998

OTHER PUBLICATIONS

Hackh's Chemical Dictionary, 4th ed. Julius Grant, ed. New York: McGraw–Hill Book Company. 1969, p. 404.*

* cited by examiner

Primary Examiner—Jeffrey E. Russel
(74) Attorney, Agent, or Firm—Thorpe North & Western, LLP

(57) ABSTRACT

A method of enhancing the solubility of iron amino acid chelates and iron proteinates is disclosed. This is accomplished by mixing an effective amount of an organic acid solubilizing agent into existing iron amino acid chelates or iron proteinates. The iron amino acid chelates and iron proteinates may have a ligand to metal molar ratio from about 1:1 to 4:1, preferably 2:1 to 3:1.

26 Claims, No Drawings

ENHANCING SOLUBILITY OF IRON AMINO ACID CHELATES AND IRON PROTEINATES

FIELD OF THE INVENTION

The present invention is drawn to methods of extending and/or improving the solubility of iron amino acid chelates and iron proteinates over longer periods of time, as well as solubilizing otherwise insoluble or less soluble iron amino acid chelates and iron proteinates.

BACKGROUND OF THE INVENTION

Amino acid chelates are generally produced by the reaction between α-amino acids and metal ions having a valence of two or more to form a ring structure. In such a reaction, the positive electrical charge of the metal ion is neutralized by the electrons available through the carboxylate or free amino groups of the α-amino acid.

Traditionally, the term "chelate" has been loosely defined as a combination of a metallic ion bonded to one or more ligands forming heterocyclic ring structures. Under this definition, chelate formation through neutralization of the positive charges of the divalent metal ions may be through the formation of ionic, covalent or coordinate covalent bonding. An alternative and more modern definition of the term "chelate" requires that the metal ion be bonded to the ligand solely by coordinate covalent bonds forming a heterocyclic ring. In either case, both definitions describe a metal ion and a ligand forming a heterocyclic ring.

A chelate is a definite structure resulting from precise requirements of synthesis. Proper conditions must be present for chelation to take place, including proper mole ratios of ligands to metal ions, pH, and solubility of reactants. For chelation to occur, all components are generally dissolved in solution and are either ionized or of appropriate electronic configuration in order for coordinate covalent bonding and/or ionic bonding between the ligand and the metal ion to occur.

Chelation can be confirmed and differentiated from mixtures of components by infrared spectra through comparison of the stretching of bonds or shifting of absorption caused by bond formation. As applied in the field of mineral nutrition, there are two allegedly "chelated" products which are commercially utilized. The first is referred to as a "metal proteinate." The American Association of Feed Control officials (AAFCO) has defined a "metal proteinate" as the product resulting from the chelation of a soluble salt with amino acids and/or partially hydrolyzed protein. Such products are referred to as the specific metal proteinate, e.g., copper proteinate, zinc proteinate, etc. Sometimes, metal proteinates are even referred to as amino acid chelates, though this characterization is not completely accurate.

The second product, referred to as an "amino acid chelate," when properly formed, is a stable product having one or more five-membered rings formed by a reaction between the amino acid and the metal. Specifically, the carboxyl oxygen and the α-amino group of the amino acid each bond with the metal ion. Such a five-membered ring is defined by the metal atom, the carboxyl oxygen, the carbonyl carbon, the α-carbon and the α-amino nitrogen. The actual structure will depend upon the ligand to metal mole ratio and whether the carboxyl oxygen forms a coordinate covalent bond or an ionic bond with the metal ion. Generally, the ligand to metal molar ratio is at least 1:1 and is preferably 2:1 or 3:1. However, in certain instances, the ratio may be 4:1. Most typically, an amino acid chelate may be represented at a ligand to metal molar ratio of 2:1 according to Formula 1 as follows:

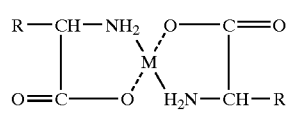

Formula 1

In the above formula, the dashed lines represent coordinate covalent bonds, covalent bonds, or ionic bonds. Further, when R is H, the amino acid is glycine which is the simplest of the α-amino acids. However, R could be representative of any other side chain resulting in any of the other twenty or so naturally occurring amino acids derived from proteins. All of the amino acids have the same configuration for the positioning of the carboxyl oxygen and the α-amino nitrogen with respect to the metal ion. In other words, the chelate ring is defined by the same atoms in each instance, even though the R side chain group may vary.

The American Association of Feed Control Officials (AAFCO) have also issued a definition for amino acid chelates. It is officially defined as the product resulting from the reaction of a metal ion from a soluble metal salt with amino acids having a mole ratio of one mole of metal to one to three (preferably two) moles of amino acids to form coordinate covalent bonds. The average weight of the hydrolyzed amino acids must be approximately 150 and the resulting molecular weight of the chelate must not exceed 800. The products are identified by the specific metal forming the chelate, e.g., iron amino acid chelate, copper amino acid chelate, etc.

The reason a metal atom can accept bonds over and above the oxidation state of the metal is due to the nature of chelation. For example, at the α-amino group of an amino acid, the nitrogen contributes both of the electrons used in the bonding. These electrons fill available spaces in the d-orbitals forming a coordinate covalent bond. Thus, a metal ion with a normal valency of +2 can be bonded by four bonds when fully chelated. In this state, the chelate can be completely satisfied by the bonding electrons and the charge on the metal atom (as well as on the overall molecule) can be zero. As stated previously, it is possible that the metal ion be bonded to the carboxyl oxygen by either coordinate covalent bonds or ionic bonds. However, the metal ion is preferably bonded to the α-amino group by coordinate covalent bonds only.

Amino acid chelates can also be formed using peptide ligands instead of single amino acids. These will usually be in the form of dipeptides, tripeptides, and sometimes, tetrapeptides because larger ligands have a molecular weight which is too great for direct assimilation of the chelate formed. Generally, peptide ligands will be derived by the hydrolysis of protein. However, peptides prepared by conventional synthetic techniques or genetic engineering can also be used. When a ligand is a di- or tripeptide, a radical of the formula $[C(O) CHRNH]_e$ H will replace one of the hydrogens attached to the nitrogen atom in Formula 1. R, as defined in Formula 1, can be H, or the residue of any other naturally occurring amino acid and e can be an integer of 1, 2 or 3. When e is 1 the ligand will be a dipeptide, when e is 2 the ligand will be a tripeptide and so forth.

The structure, chemistry and bioavailability of amino acid chelates is well documented in the literature, e.g. Ashmead et al., Chelated Mineral Nutrition, (1982), Chas. C. Thomas Publishers, Springfield, Ill.; Ashmead et al., Intestinal Absorption of Metal Ions, (1985), Chas. C. Thomas Publishers, Springfield, Ill.; Ashmead et al., Foliar Feeding of Plants with Amino Acid Chelates, (1986), Noyes Publications, Park Ridge, N.J.; U.S. Pat. Nos. 4,020,158; 4,167,564; 4,216,143; 4,216,144; 4,599,152; 4,774,089; 4,830,716; 4,863,898; 4,725,427; and others.

One advantage of amino acid chelates in the field of mineral nutrition is attributed to the fact that these chelates are readily absorbed in the gut and mucosal cells by means of active transport. In other words, the minerals can be absorbed along with the amino acids as a single unit utilizing the amino acids as carrier molecules. Therefore, the problems associated with the competition of ions for active sites and the suppression of specific nutritive mineral elements by others can be avoided. This is especially true for compounds such as iron sulfates that are typically delivered in relatively large quantities in order for the body to absorb an appropriate amount. This is significant because large quantities often cause nausea and other discomforts as well as create an undesirable taste.

In selecting an iron source for food fortification, the color and taste of the iron source is a major consideration. This is particularly true when fortifying foods that are light in color. Typically, elemental iron and iron salts have been used for food fortification, and both generally have produced off-color and off-tasting foods, depending on the amount of iron fortificant added. Because of these and other limitations, even some highly bioavailable forms of iron may not be desirable to utilize. For example, though ferrous sulfates are quite soluble with reasonable bioavailability, they often result in off-color and off-tasting foods. This is because when soluble iron salts are added to food matrixes, particularly to wet food or solutions, there is a great propensity for the iron to react with one or more components of the wet food or solution. When the iron reacts, flavors and colors can be modified. This makes the inclusion of iron into many wet foods or solutions a significant problem. Since iron fortification is desirable in many instances, even mandated by law in some instances, it would be desirable to provide an iron fortificant that may be added to food, particularly to a wet food or solution, without producing the above mentioned negative effects. Chelation can provide these advantages.

The chelation of iron with certain ligands is one alternative to maintaining iron solubility. However, selecting a ligand with a desirable stability constant is important. When iron is chelated with ascorbic acid or citric acid, the resulting stability of the chelate is relatively low. Because the stability is low, the unwanted reaction between the iron and certain food ingredients occurs. Thus, iron chelated with ligands that have a low stability constant do not provide adequate protection to the iron when mixed with food matrixes, and thus, the chelate will not retain sufficient solubility. Other chelate ligands, such as EDTA, maintain iron solubility as well and prevent the reaction of the iron cation with food ingredients. This is because the EDTA forms a chelate with iron that has a very high stability constant, thus keeping the iron in a sequestered form in the presence of various food matrixes. However, the problem associated with iron EDTA chelates, though favorably absorbed into the blood from the intestines, results from this high stability. More specifically, the stability is so high that the body cannot easily tear the iron away from the ligand. Further, if the metal ion and the EDTA ligand are separated, the EDTA is such a strong chelating agent that it can actually cause damage to the body. Therefore, even though such a chelate avoids the problems of discoloration and/or unpalatability of the fortified food, the disadvantages associated with the use of EDTA outweighs the advantages.

When iron is chelated to amino acids or small peptides, particularly with amino acid ligands at a 2:1 ligand to metal molar ratio, these ligands tend to keep the iron soluble when added to most food. The body is also able to absorb and metabolize these forms of chelates efficiently. However, the solubility of an iron amino acid chelate or iron proteinate tends to decline over time when the iron amino acid chelate or iron proteinate is added to certain foods, particularly those with a high moisture content. Further, iron amino acid chelates and iron proteinates having a ligand to metal molar ratio of about 3:1 are much less soluble than 2:1 amino acid chelates.

As such, it would be desirable to provide a method of enhancing the solubility of existing iron amino acid chelates and iron proteinates by increasing the time that the chelate remains soluble and/or solubilizing otherwise insoluble or less soluble chelates, even in the presence of a sugar such as glucose or sucrose.

SUMMARY OF THE INVENTION

A method of enhancing the solubility of iron amino acid chelates and iron proteinates is disclosed which comprises admixing an effective amount of a solubilizing agent with an iron amino acid chelate or iron proteinate having a ligand to metal molar ratio from about 1:1 to 4:1, preferably from about 2:1 to 3:1. Alternatively, a method of enhancing the solubility of an iron amino acid chelate- or iron proteinate-sugar complex comprises admixing an effective amount of an organic acid solubilizing agent into said iron amino acid chelate- or iron proteinate-sugar complex. Further, a method of enhancing the solubility of an iron amino acid chelate or iron proteinate-containing aqueous solution in the presence of a sugar comprises admixing an effective amount of an organic acid solubilizing agent into the aqueous iron amino acid chelate or iron proteinate solution prior to adding the sugar to the solution.

DETAILED DESCRIPTION OF THE INVENTION

Before the present invention is disclosed and described, it is to be understood that this invention is not limited to the particular process steps and materials disclosed herein because such process steps and materials may vary somewhat. It is also to be understood that the terminology used herein is used for the purpose of describing particular embodiments only. The terms are not intended to be limiting because the scope of the present invention is intended to be limited only by the appended claims and equivalents thereof.

It must be noted that, as used in this specification and the appended claims, the singular forms "a," "an," and "the" include plural referents unless the content clearly dictates otherwise.

The phrase "enhancing the solubility" refers to improving the solubility of existing iron amino acid chelates and iron proteinates, even in the presence of a sugar, or when complexed to a sugar. This may be manifest by extending the solubility time of a soluble iron amino acid chelate or iron proteinate or solubilizing an otherwise insoluble or less soluble iron amino acid chelate or iron proteinate.

The term "amino acid chelate" is intended to cover both the traditional definitions and the more modern definition of chelate as cited previously. Specifically, for purposes of the present invention, chelate is meant to include metal ions bonded to amino acids or proteinaceous ligands forming heterocyclic rings. The bonds may be coordinate covalent, covalent, and/or ionic at the carboxyl oxygen group.

However, at the α-amino group, the bond is typically a coordinate covalent bond.

The term "proteinate" when referring to an iron proteinate is meant to include compounds where iron is chelated or complexed to hydrolyzed or partially hydrolyzed protein forming a heterocyclic ring. Coordinate covalent bonds, covalent bonds and/or ionic bonding may be present in the chelate or chelate/complex structure.

The method of the present invention involves the enhancing of the solubility of iron amino acid chelates and iron proteinates by (a) prolonging of the solubility of a soluble iron amino acid chelate or proteinate and/or (b) solubilizing an otherwise insoluble or less soluble iron amino acid chelate or proteinate. The method of enhancing the solubility of iron amino acid chelates and iron proteinates comprises admixing an effective amount of a solubilizing agent with one or more iron amino acid chelate or iron proteinate having a ligand to metal molar ratio from about 1:1 to 4:1, preferably from about 2:1 to 3:1. The organic acid solubilizing agent can be selected from the group consisting of acetic acid, ascorbic acid, citric acid, lactic acid, malic acid, succinic acid, and combinations thereof.

To illustrate several preferred embodiments, the following guidelines are useful in determining how much of each organic acid can be added to the iron chelates in order to enhance solubility. If ascorbic acid is being added to the iron amino acid chelate or iron proteinate, the ascorbic acid to iron content ratio can be from about 5:1 to 1:1 by weight. If citric acid is being added to the iron amino acid chelate or iron proteinate, the citric acid to iron content ratio can be from about 3:1 to 1:1 by weight. Likewise, for acetic acid, the organic acid to iron content ratio can be from about 3:1 to 1:1 by weight; for lactic acid, the organic acid to iron content ratio can be from about 3:1 to 1:1 by weight; for malic acid, the organic acid to iron content ratio can be from about 3:1 to 1:1 by weight; and for succinic acid, the organic acid to iron content ratio can be from about 3:1 to 1:1 by weight.

Though these ratios ranges are useful in practicing the invention, the invention is not limited by their values. Any of these organic acids could be used outside of these preferred ranges with a more limited usefulness. Further, acids may be combined. For example, ascorbic acid and citric acid may be added in combination having an ascorbic acid to citric acid molar ratio from about 10:1 to 1:1, and wherein the total solubilizing agent to iron content weight ratio is from about 5:1 to 1:1.

Preferably, the iron amino acid chelate or iron proteinate and the solubilizing agent can be homogeneously mixed together in particulate form to be subsequently hydrated for food fortification. However, the iron amino acid chelate or iron proteinate and the solubilizing agent may be hydrated prior to the mixing step, forming a liquid mixture rather than a particulate mixture. Further, other combinations are also possible such as mixing the iron amino acid chelate or iron proteinate in a particulate form with the solubilizing agent in a liquid form, or conversely, mixing the iron amino acid chelate or iron proteinate in a liquid form with the solubilizing agent in a particulate form.

A method of enhancing the solubility of an iron amino acid chelate- or iron proteinate-sugar complex is also disclosed which comprises admixing an effective amount of an organic acid solubilizing agent into an iron amino acid chelate- or iron proteinate-sugar complex. The iron amino acid chelate- or iron proteinate-sugar complex to be solubilized generally comprises iron, an amino acid or proteinate ligand, and a sugar such as glucose and/or sucrose.

Additionally, a method of enhancing the solubility of an iron amino acid chelate or iron proteinate-containing aqueous solution in the presence of a sugar is disclosed which comprises admixing an effective amount of an organic acid solubilizing agent into the aqueous iron amino acid chelate or iron proteinate solution prior to adding sugar to the solution.

In both of these methods involving an iron amino acid chelate or iron proteinate and a sugar, the ligand to iron molar ratio can be from about 1:1 to 4:1, preferably 2:1 to 3:1, and the sugar to iron content molar ratio can be from about 1:1 to 3:1. Again, the solubilizing agent may be selected from the group consisting of citric acid, ascorbic acid, acetic acid, lactic acid, malic acid, succinic acid, and combinations thereof, and the solubilizing agent to iron content weight ratio can be from about 4:1 to 1:1.

EXAMPLES

The following examples illustrate this preparative method. The following examples should not be considered as limitations of the present invention, but should merely teach how to make the best known amino acid chelates based upon current experimental data.

Example 1

Ferrous iron was chelated in solution by glycine at a glycine to iron molar ratio of 2:1 (ferrous bisglycinate). The chelate was dried by spray drying. The final chelate contained 18% iron. The dried iron amino acid chelate was divided into two samples. Sample 1 acted as the control. Sample 2 was mixed with ascorbic acid at a rate of 30% ascorbic acid to 70% iron amino acid chelate by weight. To show that the inclusion of ascorbic acid promotes solubility of iron amino acid chelates, Sample 1 was compared with Sample 2 in two phases.

Phase 1

After hydrating Sample 1 and Sample 2 with an amount of water sufficient to dissolve the respective powders and allowing 4 hours to pass, a small amount of each solution was placed on filter paper with a pipette. By placing the two solutions on paper in this manner, the respective solutions were allowed to disperse away from the point of application while leaving behind any solids that may have formed. The iron amino acid chelate of Sample 1 left behind a small clump of precipitate. The iron amino acid chelate of Sample 2 left no visual precipitate behind.

Phase 2

Both remaining solutions were retained in test tubes for 20 additional hours. At the end of that time, a visual examination of the two samples indicated that approximately 50% of Sample 1 had precipitated from solution. Conversely, Sample 2 remained in solution.

Example 2

Ferric iron was chelated by glycine in solution at a glycine to iron molar ratio of 3:1 (ferric trisglycinate). The chelate was dried by spray drying. The final chelate contained 19% iron. Typically, this type of iron amino acid chelate has very little solubility. A mixture of ferric trisglycinate (95% by weight) and citric acid (5% by weight) was prepared. This mixture was then added to an excess of water and left standing. About 24 hours later, 50% of the once insoluble chelate had gone into solution.

Example 3

Iron bisglycinate was prepared and used to determine which organic acids aided in enhancing the solubility of iron amino acid chelates. Glucose and sucrose were also tested likewise. The iron bisglycinate was then hydrated, and a pH level of about 8 was measured. The aqueous iron bisglycinate was then placed on filter paper with a pipette and the rings were characterized after drying. Staggered brown rings were formed (after the droplet dried) from the center and in an outward direction. However, no notable rings were formed at the location where the waterfront had existed.

After characterizing the iron bisglycinate as a control, citric acid, ascorbic acid, acetic acid, lactic acid, malic acid, and succinic acid were added to separate samples of the iron bisglycinate. Each showed enhancement of mobility and solubility on the filter paper. Conversely, the addition of sugars to the iron bisglycinate decreased solubility as characterized by a visual inspection. The results of the visual inspection and filter paper characterization of each potential solubilizing agent are illustrated by Table 1 as follows:

TABLE 1

| COMPOUND ADDED | pH | VISUAL | RING APPEARANCE |
|---|---|---|---|
| Ascorbic Acid | 6.0 | no precipitation | dark waterfront ring |
| Acetic Acid | 3.5 | no precipitation | dark waterfront ring |
| Citric Acid | 4.5 | no precipitation | dark waterfront ring |
| Lactic Acid | 6.0 | no precipitation | dark waterfront ring |
| Malic Acid | 6.0 | no precipitation | dark waterfront ring |
| Succinic Acid | 6.0 | no precipitation | dark waterfront ring |
| Glucose | 7.0 | precipitated solids | light staggered ring |
| Sucrose | 7.0 | precipitated solids | light staggered ring |

In Table 1, the ratio of each of the listed compounds to iron content was about 1.8:1 by weight. The pH value describes the pH level of the solution at this ratio.

Table 1 above shows that the mobility and solubility of the iron bisglycinate in water, even at low pH levels, was enhanced with the addition of organic acids as solubilizing agents as is evidenced by the appearance of darker rings corresponding to the location of the waterfront (after drying). Conversely, the addition of sugars decreased the solubility as is shown by the visual presence of precipitated solids.

Though not shown in Table 1, when one of the organic acids is added to an iron amino acid chelate-sugar precipitate, the solids dissolve back into solution. Further, when one of the organic acids is added to an iron amino acid chelate prior to the addition of any sugar, a precipitate will not form when the sugar is added. This suggests that a solution containing an iron amino acid chelate is stable in an organic acid-sugar environment such as that found in fruit or in juice.

Example 4

An iron proteinate or iron protein hydrolysate which was hydrolyzed from a vegetable protein was formed having an iron content of about 10%. The proteinate was hydrated and the pH measured at about 3.0. Visually, the color of the solution was brown and contained particulates. A small amount of the solution was placed on filter paper with a pipette. When the water evaporated, brown staggered rings were left behind.

Next, several different organic acids and sugars were added to various samples of the solution. Each was inspected both visually and by placing a small amount of solution on filter paper with a pipette. Table 2 below illustrates what was observed:

TABLE 2

| COMPOUND | pH | VISUAL | RING APPEARANCE |
|---|---|---|---|
| Ascorbic Acid | 4.5 | no change | dark brown waterfront ring |
| Acetic Acid | 3.0 | no change | dark brown waterfront ring |
| Citric Acid | 1.5 | no change | dark brown waterfront ring |
| Lactic Acid | 1.0 | no change | dark brown waterfront ring |
| Malic Acid | 2.0 | no change | dark brown waterfront ring |
| Succinic Acid | 2.0 | no change | dark brown waterfront ring |
| Glucose | 7.0 | no change | brown staggered rings |
| Sucrose | 7.0 | no change | brown staggered rings |

In Table 1, the ratio of each of the listed compounds to iron content was about 1:1 by weight. The pH value describes the pH level of the solution at this ratio.

Table 2 above shows that the mobility and solubility of the iron proteinate in water, even at low pH levels, was enhanced with the addition of organic acids as solubilizing agents. This is evidenced by darker rings remaining on the filter paper which corresponded to location of the waterfront. However, the rings left behind after adding glucose or sucrose were similar to the control iron proteinate rings.

The above examples show that the addition of ascorbic acid, citric acid, acetic acid, malic acid and or succinic acid help iron amino acid chelates and iron proteinates retain their solubility, or alternatively, aid in solubilizing otherwise insoluble or less soluble forms of iron amino acid chelates and iron proteinates. Further, even in the presence of a sugar such as glucose or sucrose, the organic acid solubilizing agents enhance the solubility of the iron amino acid chelate- and iron proteinate-sugar complexes.

We claim:

1. A method of enhancing the solubility of iron amino acid chelates and iron proteinates comprising admixing an effective amount of an organic acid solubilizing agent with an iron amino acid chelate or iron proteinate having a ligand to metal molar ratio from about 1:1 to 4:1 to form a mixture of iron amino acid chelate or iron proteinate and organic acid, wherein the solubilizing agent to iron content weight ratio is from about 5:1 to 1:1.

2. A method as in claim 1 wherein the ligand to metal molar ratio is from about 2:1 to 3:1.

3. A method according to claim 1 wherein said solubilizing agent is selected from the group consisting of citric acid, ascorbic acid, acetic acid, lactic acid, malic acid, succinic acid, and combinations thereof.

4. A method according to claim 1 wherein said solubilizing agent is acetic acid and wherein the acetic acid to iron content weight ratio is from about 3:1 to 1:1.

5. A method according to claim 1 wherein said solubilizing agent is ascorbic acid and wherein the ascorbic acid to iron content weight ratio is from about 5:1 to 1:1.

6. A method according to claim 1 wherein said solubilizing agent is citric acid and wherein the citric acid to iron content weight ratio is from about 3:1 to 1:1.

7. A method according to claim 1 wherein said solubilizing agent is lactic acid and wherein the lactic acid to iron content weight ratio is from about 3:1 to 1:1.

8. A method according to claim 1 wherein said solubilizing agent is malic acid and wherein the malic acid to iron content weight ratio is from about 3:1 to 1:1.

9. A method according to claim 1 wherein said solubilizing agent is succinic acid and wherein the succinic acid to iron content weight ratio is from about 3:1 to 1:1.

10. A method according to claim 1 wherein said solubilizing agent is a combination of ascorbic acid and citric acid at a molar ratio from 10:1 to 1:1, and wherein the iron content to solubilizing agent ratio is from about 5:1 to 1:1 by weight.

11. A method according to claim 1 wherein said iron amino acid chelate or iron proteinate and said solubilizing agent are in a particulate form and wherein said mixing step produces a particulate homogenous mixture prior to hydration.

12. A method according to claim 11 wherein said particulate mixture is hydrated.

13. A method according to claim 1 wherein said iron amino acid chelate or iron proteinate and said solubilizing agent are hydrated prior to said admixing step.

14. A method according to claim 1 wherein said iron amino acid chelate or iron proteinate is in a particulate form and wherein said solubilizing agent is in a liquid form when admixed.

15. A method according to claim 1 wherein said iron amino acid chelate or iron proteinate is in a liquid form and wherein said solubilizing agent is in a particulate form when mixed.

16. A method of enhancing the solubility of an iron amino acid chelate- or iron proteinate-sugar complex comprising admixing an effective amount of an organic acid solubilizing agent into said iron amino acid chelate- or iron proteinate-sugar complex to form a mixture of iron amino acid chelate- or iron proteinate-sugar complex and organic acid, wherein the solubilizing agent to iron content ratio is from about 4:1 to 1:1 by weight.

17. A method according to claim 16 wherein said iron amino acid chelate- or iron proteinate-sugar complex comprises iron, an amino acid or proteinate ligand, and a sugar, wherein said ligand to iron molar ratio is from about 1:1 to 4:1 and wherein said sugar content to said iron content molar ratio is from about 1:1 to 3:1.

18. A method according to claim 17 wherein said ligand to iron molar ratio is from about 2:1 to 3:1.

19. A method according to claim 17 wherein said solubilizing agent is selected from the group consisting of citric acid, ascorbic acid, acetic acid, lactic acid, malic acid, succinic acid, and combinations thereof.

20. A method according to claim 17 wherein said sugar is selected from the group consisting of glucose, sucrose, and combinations thereof.

21. A method of enhancing the solubility of an iron amino acid chelate or iron proteinate-containing aqueous solution in the presence of a sugar comprising admixing an effective amount of an organic acid solubilizing agent into said iron amino acid chelate or iron proteinate aqueous solution to form a mixture of iron amino acid chelate or iron proteinate and organic acid prior to adding said sugar to said solution.

22. A method according to claim 21 wherein said iron amino acid chelate or iron proteinate has a ligand to iron molar ratio from about 1:1 to 4:1 and wherein said sugar content to said iron content molar ratio is from about 1:1 to 3:1.

23. A method according to claim 22 having a ligand to iron molar ratio from about 2:1 to 3:1.

24. A method according to claim 21 wherein said solubilizing agent is selected from the group consisting of citric acid, ascorbic acid, acetic acid, lactic acid, malic acid, succinic acid, and combinations thereof.

25. A method according to claim 21 wherein the solubilizing agent to iron content ratio is from about 4:1 to 1:1 by weight.

26. A method according to claim 21 wherein said sugar is selected from the group consisting of glucose, sucrose, and combinations thereof.

\* \* \* \* \*